United States Patent
Weigert et al.

(10) Patent No.: US 10,618,946 B2
(45) Date of Patent: Apr. 14, 2020

(54) N-TERMINALLY TRUNCATED INTERLEUKIN-38

(71) Applicant: FRAUNHOFER-GESELLSCHAFT ZUR FÖRDERUNG DER ANGEWANDTEN FORSCHUNG E.V., Munich (DE)

(72) Inventors: Andreas Weigert, Hofheim am Taunus (DE); Javier Mora, Frankfurt am Main (DE); Bernhard Brune, Schöneck (DE); Christina Dillmann, Frankfurt (DE); Michael John Parnham, Bad Soden am Taunus (DE); Gerd Geisslinger, Bad Soden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/328,690

(22) PCT Filed: Jul. 14, 2015

(86) PCT No.: PCT/EP2015/066084
§ 371 (c)(1),
(2) Date: Jan. 24, 2017

(87) PCT Pub. No.: WO2016/012312
PCT Pub. Date: Jan. 28, 2016

(65) Prior Publication Data
US 2017/0218039 A1   Aug. 3, 2017

(30) Foreign Application Priority Data
Jul. 25, 2014   (EP) .................................... 14178478

(51) Int. Cl.
*C07K 14/52* (2006.01)
*C07K 14/54* (2006.01)
*G01N 33/68* (2006.01)
*G01N 33/50* (2006.01)
*A61K 38/00* (2006.01)

(52) U.S. Cl.
CPC ......... *C07K 14/54* (2013.01); *G01N 33/5041* (2013.01); *G01N 33/6869* (2013.01); *A61K 38/00* (2013.01); *G01N 2333/54* (2013.01); *G01N 2500/10* (2013.01)

(58) Field of Classification Search
None
See application file for complete search history.

(56) References Cited

U.S. PATENT DOCUMENTS 7,374,911 B2 * 5/2008 Labow .................. C07K 14/545
435/320.1

FOREIGN PATENT DOCUMENTS

| JP | 2003-523209 A | 8/2003 |
|---|---|---|
| JP | 2010-131026 A | 6/2010 |
| WO | 01/40291 | 6/2001 |
| WO | 01/55211 | 8/2001 |

OTHER PUBLICATIONS

"Myotis davidii unplaced genomic scaffold scaffold165, whole genome shotgun sequence.", XP002734155, retrieved from EBI accession No. EMBL: KB112867, Database accession No. EMBL: KB112867, 6 pages; sequence, Dec. 23, 2012.
"*Ailuropoda melanoleuca* (giant panda) partial hypothetical protein", XP002734156, retrieved from EBI accession No. EFB23354, Database accession No. EFB23354, 16 pages; sequence, Dec. 19, 2009.
XP002734157 Retrieved from Uniprot, Database accession No. UPI0000207D75, the whole document, 1 page, Mar. 23, 2007.
Garlanda et al., "The Interleukin-1 Family: Back to the Future", Immunity, vol. 39, No. 6, Dec. 1, 2013, pp. 1003-1018, XP055160331.
Van De Veerdonk et al., "IL-38 binds to the IL-36 receptor and has biological effects on immune cells similar to IL-36 receptor antagonist", Proceedings of the National Academy of Sciences of the United States of America, vol. 109, No. 8, Feb. 2012, pp. 3001-3005, XP002734158.
International Search Report and Written Opinion, International Patent Application No. PCT/EP2015/066084, dated Sep. 28, 2015 (14 pages).
Office Action, Japanese Patent Application No. 2016-574256, dated Oct. 18, 2018, with English translation (21 pages).
Database GenBank [online], Accession No. KB112867, Dec. 20, 2012 uploaded, [retrieved on Oct. 10, 2018], < https://www.ncbi.nlm.nih.gov/nuccor e/KB112867.1?report=gbwithparts&log$=seqview&sat=21&satkey = 20315030>, Definitions: Myotis davidii unplaced genomic scaffold scaffold165, whole genome shotgun sequence.
Database GenBank [online], Accession No. GL193421,Dec. 17, 2009 uploaded, [retrieved on Oct. 10, 2018], < https://www.ncbi.nlm.nih.gov/nuccore/GL193421.1?report=gbwithparts&log$=seqview&sat=16&satkey = 8249030>, Ailuropoda melanoleuca unplaced genomic scaffold scaffold3406, a whole genome shotgun sequence.

* cited by examiner

*Primary Examiner* — Celine X Qian
(74) *Attorney, Agent, or Firm* — Hamre, Schumann, Mueller & Larson, P.C.

(57) ABSTRACT

The present invention pertains to an N-terminally truncated interleukin (IL)-38 protein, or functional variants thereof, as well as to nucleic acids and vectors encoding the truncated IL-38 peptide and recombinant cells comprising these nucleic acids or vectors. The invention shows that IL-38 is N-terminally processed and that the truncated version of the cytokine acts as an antagonist of immune activation in macrophages. This indicates a use of the truncated cytokine in the treatment and prevention of autoimmune disorders. The invention further provides pharmaceutical compositions comprising the truncated IL-38 protein, and method for screening modulators of the function of truncated IL-38.

Figure 1:
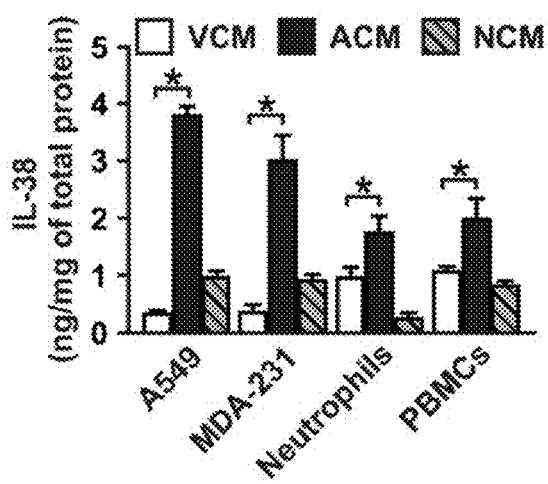
Figure 1:
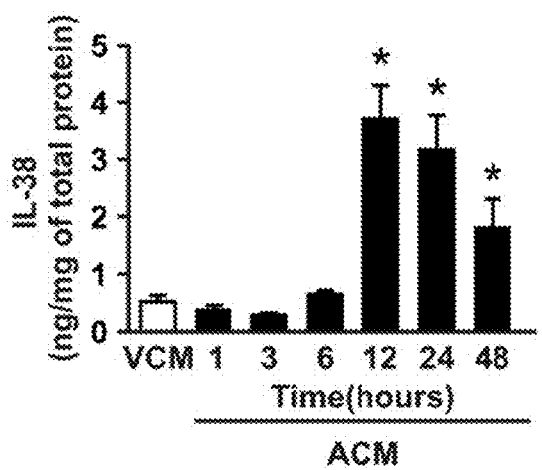

1 Claim, 9 Drawing Sheets
Specification includes a Sequence Listing.

N-TERMINALLY TRUNCATED INTERLEUKIN-38

FIELD OF THE INVENTION

The present invention pertains to an N-terminally truncated interleukin (IL)-38 protein, or functional variants thereof, as well as to nucleic acids and vectors encoding the truncated IL-38 peptide and recombinant cells comprising these nucleic acids or vectors. The invention shows that IL-38 is N-terminally processed and that the truncated version of the cytokine acts as an antagonist of immune activation in macrophages. This indicates a use of the truncated cytokine in the treatment and prevention of autoimmune disorders. The invention further provides pharmaceutical compositions comprising the truncated IL-38 protein, and method for screening modulators of the function of truncated IL-38.

DESCRIPTION

The IL-1 family of cytokines and receptors is a heterogeneous group of proteins that particularly regulate immunity. Initially, four IL-1 family cytokines were intensively characterized (IL-1α, IL-1β, IL-1Ra and IL-18), revealing basal principles of immune regulation, some of which were already translated into the clinic. The remaining seven IL-1 family cytokines were identified by in silico analysis of gene databases (IL-33, IL-36α, IL-36β, IL-36γ, IL-36Ra, IL-37 and IL-38). In recent years, important studies were conducted to investigate their relevance for induction or regulation of the immune response. Conclusively, IL-1 family cytokines exhibit a broad spectrum of functions in immunity, including the induction of Th1 and Th2 inflammation as well as mediating anti-inflammatory or pro-resolving effects. On a mechanistic level, triggering of inflammation is mediated by IL-1 family cytokines with receptor agonist (IL-1α, IL-1β, IL-18, IL-33, IL-36) function, which is counteracted by IL-1 family receptor antagonists (IL-1Ra, IL-36Ra). Of note, full receptor agonistic or antagonistic function often requires N-terminal processing of IL-1 family cytokines, usually creating the mature cytokine from a precursor. The most prominent of these events is probably IL-1β maturation by the inflammasome.

IL-1 family receptors are characterized by the presence of extracellular immunoglobulin domains and an intracellular TIR domain that is necessary for signal transduction. The IL-1 receptor family includes four members with known ligand and function: IL-1R1 (IL-1RI), IL-1R4 (ST2), IL-1R5 (IL-18R), IL-1R6 (IL-1Rrp2); two co-receptors: IL-1R3 (IL-1RAcP), IL-1R7 (IL-18AcP); one decoy receptor: IL-1R2 (IL-1RII); and three orphan receptors TIR8 (SIGIRR), TIGIRR-1 (IL-1RAPL2), TIGIRR-2 (IL-1RAPL1). The nomenclature of the orphan receptors is still ambiguous. IL-1RAPL1, also known as TIGIRR-2, was originally named IL-1R8. However, it was recently referred to as IL-1R9 or IL-1R10. To avoid confusion, the inventors will use the term IL-1RAPL1 in the present manuscript. IL-1RAPL1 is highly expressed in the brain and is involved in cerebellar development, mental retardation and cognitive defects. The main structural difference to other members of the IL-1 receptor family is a C-terminal 150 amino acid-long extension in the intracellular domain of IL-1RAPL1, which is also present in its close homolog IL-1RAPL2 and the regulatory receptor TIR8. A role of this structure in cellular signaling has not been described. Functional studies suggest that the mechanism of activation and downstream signaling of IL-1RAPL1 differs from that of other members of the IL-1 receptor family. There is evidence that IL-1RAPL1 selectively activates JNK, which is, among others, involved in immune activation. Indeed, a functional RNAi screen revealed that IL-1RAPL1 regulates the macrophage phenotype upon interaction with apoptotic cells.

IL-38, also known as IL-1F10, is the most recent addition to the IL-1 family. It shares 41% homology with IL-1Ra and 43% with IL-36Ra and was therefore proposed as an IL-1 receptor antagonist. Indeed, it has been recently shown that IL-38 can bind to IL-1R6, where it reduces cytokine production after *C. albicans* stimulation or addition of IL-36 when administered at low concentrations. Nevertheless, an increase in cytokine produced was noted after LPS stimulation together with IL-38. In general IL-38 polymorphisms are associated with increased susceptibility to develop autoinflammatory pathologies such as spondyloarthritis, rheumathoid arthritis or psoriatic arthritis or with CRP levels, suggesting a role of IL-38 in the regulation of the mechanisms underlying such conditions.

Cytokines include a large number of mammalian immunoregulatory hormones that are secreted by cells of the immune system. They exert their biological effects through interaction with specific receptors on cell surfaces. Therefore, the biological response to a cytokine is regulated both by the presence of the cytokine and by the expression of its receptor molecule. Many mammalian diseases, including autoimmune, inflammatory and cancer diseases, are correlated with increased or otherwise altered levels of cytokines or cytokine receptors which may contribute to the misregulation of the immune system and to disease progression. Compounds which are capable of blocking the immunoregulatory or inflammatory effects of cytokines should therefore have significant therapeutic activity with respect to such disease states.

Conventional strategies for generating immunosuppression associated with an undesired immune response are based on broad-acting immunosuppressive drugs. Additionally, in order to maintain immunosuppression, immunosuppressant drug therapy is generally a life-long proposition. Unfortunately, the use of broad-acting immunosuppressants is associated with a risk of severe side effects, such as tumors, infections, nephrotoxicity and metabolic disorders. Accordingly, new immunosuppressant therapies would be beneficial.

Hence, until this day there is no satisfactory therapeutic approach for treating or preventing autoimmune disease and there is a constant need for additional immunosuppressive agents in order to advance medical care for patients suffering from diseases associated with a pathological or even chronically activated immune system.

The above problem is solved in a first aspect by an isolated truncated IL-38 protein, or a functional variant thereof, wherein said truncated IL-38 protein is N-terminally truncated compared to the amino acid sequence according to SEQ ID NO: 1.

As used herein, the term "truncated IL-38 protein" refers to an IL-38 polypeptide in which amino acid residues have been removed from the amino-terminal (or N-terminal) area of the full length IL-38 polypeptide. A "truncated IL-38 protein" in the context of the present invention never comprises the full-length sequence as shown in SEQ ID NO: 1.

The term "functional variant" of a protein means herein a variant protein, wherein the function, in relation to the invention defined as affinity and stability, is essentially retained. Thus, one or more amino acids that are not relevant for said function may have been exchanged. The term 'functional variant' should also be understood to mean homologues from other mammals. Preferably the functional variants of the present invention retain the immune suppressive abilities of the herein described truncated IL-38 protein as shown in SEQ ID NO: 2.

In a preferred embodiment the isolated truncated IL-38 protein, or functional variant thereof, comprises an amino acid sequence having at least 50% sequence identity to the amino acid sequence according to SEQ ID NO: 1 (full length IL-38), characterized in that the truncated IL-38 protein does not comprise the full length amino acid sequence shown in SEQ ID NO: 1.

The term "sequence identity" (or "sequence homology") indicates a quantitative measure of the degree of identity between two amino acid sequences of equal length or between two nucleotide sequences of equal length. If the two sequences to be compared are not of equal length, they must be aligned to the best possible fit with the insertion of gaps or alternatively truncation at the ends of the protein sequences.

A more preferred minimum percentage of sequence identity is at least 70%, such as at least 80%, at least 85%, at least 90%, at least 91%, at least 92%, at least 93%, at least 94%, at least 95%, at least 96%, at least 97%, at least 98%, at least 99%, and at least 99.5%, most preferably 100% compared to the sequence shown in SEQ ID NO:1, under the proviso that said truncated IL-38 sequence does not comprise the IL-38 full length sequence as shown in SEQ ID NO: 1.

Said truncated IL-38 protein of the invention has in a preferred embodiment 2-50 amino acids, truncated at its N-terminus, as compared with wild type IL-38 protein (SEQ ID NO: 1). Preferably said truncated IL-38 protein has 9, 10 11, 12, 13, 14, 15, 16, 17, 18, 19 or 20 amino acids truncated at its N-terminal as compared to the protein shown in SEQ ID NO: 1. Most preferred are 19.

The N-terminal truncation in accordance to the herein described invention preferably involves at least 2, preferably 5, most preferably 10, most preferably 20 adjoining amino acids between positions 1 to 30 of SEQ ID NO: 1.

In other embodiments the truncated IL-38 protein of the invention has an N-terminus that is not identical to the first 100, 50, 30, 20 amino acids of SEQ ID NO: 1.

In other embodiments the truncated IL-38 protein of the invention has an N-terminus, wherein the first 50 amino acids of the N-terminal end are not identical to the first 50 amino acids of SEQ ID NO: 1.

In other embodiments the truncated IL-38 protein of the invention has an N-terminus, wherein the first 20 amino acids of the N-terminal end are not identical to the first 20 amino acids of SEQ ID NO: 1.

Alternatively a truncated IL-38 protein of the invention does not comprise a sequence that is at least 80% identical to the sequence between positions 1 to 20 of SEQ ID NO: 1.

Yet most preferred is a truncated IL-38 protein, consisting of an amino acid sequence having at least 80%, 85%, 90%, 95% or 100% sequence identity to SEQ ID NO: 2 (20-152_IL-38). If produced by recombinant expression of a truncated IL-38 protein of the invention, the sequence of the truncated IL-38 protein is characterized by the presence of an additional methionine at the N-terminus. Such proteins may be after expression subjected to a purification process to obtain isolated truncated IL-38 protein of the invention.

"Isolated" and "purified" refer to any molecule or compound that is separated from its natural environment and is from about 60% to about 99% free, preferably 80% to 99% free from other components with which it is naturally associated.

Therefore, in this respect particularly preferred truncated IL-38 proteins of the invention comprise an N-terminal methionine at position 1; such proteins are purely artificial and not present in nature.

The term "recombinant" as used herein refers to a protein or nucleic acid construct, generated recombinantly or synthetically, e.g., in the case of a protein, through the translation of the RNA transcript of a particular vector- or plasmid-associated series of specified nucleic acid elements or of an expression cassette in a host cell. The term "recombinant" as used herein does not encompass the alteration of the cell or vector by naturally occurring events (e.g., spontaneous mutation, natural transformation/transduction/transposition) such as those occurring without deliberate human intervention.

By "host cell" is meant a cell, which contains a vector or expression cassette and supports the replication and/or expression thereof. Host cells may be prokaryotic cells such as *E. coli*, or eukaryotic cells such as yeast, insect, amphibian, plant cells or mammalian cells. Preferably, host cells are bacterial or prokaryotic cells.

As used herein, "vector" includes reference to a nucleic acid used in transfection of a host cell and into which can be inserted a polynucleotide. Vectors are often replicons.

The term "protein" or "proteins" as used herein refers to a polypeptide or any portion thereof.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as the modifications known in the art, both naturally occurring and non-naturally occurring.

The term "recombinant protein" as used herein refers to (1) a polypeptide of semisynthetic or synthetic origin resulting from the expression of a combination of DNA molecules of different origin that are joined using recombinant DNA technologies; (2) a polypeptide of semisynthetic or synthetic origin that, by virtue of its origin or manipulation, is not associated with all or a portion of a protein with which it is associated in nature; (3) a polypeptide of semisynthetic or synthetic origin that is linked to a polypeptide other than that to which it is linked in nature; or (4) a polypeptide of semisynthetic or synthetic origin that does not occur in nature.

The present invention also contemplates chemically or otherwise modified truncated IL-38 proteins. Modified versions of the herein described polypeptides are for example IL-38 proteins which were post-translational modified. A post-translational modification may be the glycosylation of the expressed protein.

The above described problem of the prior art is in one additional aspect thereof solved by providing a nucleic acid comprising a sequence coding (or encoding) for a truncated IL-38 protein as described herein. The term "coding" or "encoding" refers to the ability of a nucleotide sequence to code for one or more amino acids. The term does not require a start or stop codon. An amino acid sequence can be encoded in any one of six different reading frames provided by a polynucleotide sequence and its complement.

The nucleic acid of the invention may comprise a sequence that when expressed produces a polypeptide consisting of the truncated IL-38 protein of the invention, but which is not the full length IL-38 protein according to SEQ ID NO: 1.

Yet another aspect of the invention pertains to a vector comprising a nucleic acid as described herein before. Most preferred is that the vector of the invention is an expression vector.

An "expression vector" is a nucleic acid construct or sequence, generated recombinantly or synthetically, with specific nucleic acid elements that permit transcription and/or expression of another nucleic acid in a host cell. An expression vector can be part of a plasmid, virus, or nucleic acid fragment. In one example, an expression vector is a DNA vector, such as a plasmid, that comprises at least one promoter sequence and at least one terminator sequence (e.g., a polyadenylation sequence), and optionally an origin of replication (ori) sequence, and optionally a selection or selectable marker sequence. Optionally, the expression vector may further comprise at least one nucleotide coding sequence of interest that codes for at least one polypeptide, wherein the at least one promoter sequence is operably linked with the at least one coding sequence. The term "expression" includes any step involved in the production of the polypeptide including, but not limited to, transcription, post-transcriptional modification, translation, post-translational modification, and/or secretion.

Also provided is a recombinant cell, comprising a nucleic acid or a vector or expression vector as described herein. A recombinant cell of the invention is preferably not a human embryonic stem cell. Preferred recombinant cells of the invention are for example bacterial cells such as E. coli or other expression systems, or also animal cells such as insect cells, mammalian cells and human cells.

The compounds and compositions as described herein may be applied in various medical fields, in particular as active therapeutics in the treatment or prevention of a disease characterized by the pathological activation of the immune response in a subject in need of such a treatment. Preferred disease to be treated by the compounds of the invention will be described herein below.

Hence, in an additional aspect the invention also provides a pharmaceutical composition comprising a truncated IL-38 protein, or a nucleic acid, a vector or a recombinant cell according to the afore described embodiments of the invention, for use in medicine, preferably for use in the treatment or prevention of an immune- or inflammatory disease.

In context of the present invention an immune or inflammatory disease is preferably selected from autoimmune diseases, such as septic shock, hemorrhagic shock, arthritis, for example spondyloarthritis, rheumatoid arthritis, psoriatic arthritis or osteoarthritis, inflammatory bowel disease, multiple sclerosis and metabolic diseases such as arteriosclerosis and type I diabetes. Further indications include those responsive to treatment with inhibitors of IL-1β, such as Muckle-Wells syndrome, cryopyrin-associated periodic fever syndromes (CAPS), familial Mediterranean fever, Still's disease, Behçet's disease and diabetes mellitus.

Arthritis, including osteoarthritis, rheumatoid arthritis, arthritic joints as a result of injury or crystal deposits, and the like, are common inflammatory conditions which would benefit from the therapeutic use of the anti-inflammatory proteins, such as truncated IL-38 proteins of the present invention. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, Expert. Opin. Biol. Ther. 2(2):135-149. 2002; Astry, J. Interferon Cytokine Res. 31(12):927-40. 2011).

For pharmaceutical use, the truncated IL-38 proteins of the invention are formulated for parenteral, particularly intravenous or subcutaneous, delivery according to conventional methods. Intravenous administration will be by bolus injection, controlled release, e.g, using minipumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. When utilizing such a combination therapy, the cytokines may be combined in a single formulation or may be administered in separate formulations. Methods of formulation are well known in the art and are disclosed, for example, in Remington's Pharmaceutical Sciences. Gennaro, ed., Mack Publishing Co., Easton Pa., 1990, which is incorporated herein by reference.

Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days. More commonly, the proteins will be administered over one week or less, often over a period of one to three days. In general, a therapeutically effective amount of truncated IL-38 protein of the present invention is an amount sufficient to produce a clinically significant decrease of the pathological inflammatory response.

Generally, the dosage of administered truncated IL-38 protein will vary depending upon such factors as the patient's age, weight, height, sex, general medical condition and previous medical history. Typically, it is desirable to provide the recipient with a dosage of truncated IL-38 protein which is in the range of from about 1 pg/kg to 10 mg/kg (amount of agent/body weight of patient), although a lower or higher dosage also may be administered as circumstances dictate. Specific embodiments of the pharmaceutical compositions of the invention are provided herein below.

In an additional aspect the present invention provides a method of treating or preventing a pathological inflammatory disorder in a subject in need of such a treatment. The method of the invention may comprise the step of administering to said subject a therapeutically active amount of any one of the herein described compounds or compositions of the invention.

Another aspect of the invention pertains to a method for modulating the immune response of a cell, the method comprising contacting said cell with a truncated IL-38 protein of the invention, or by expressing in said cell a nucleic acid according to the invention.

In a preferred embodiment the method is an ex-vivo or in-vitro method.

A "modulating the immune response" may be an inhibition of JNK signalling, in particular the inhibition of IL-6 release and TH17 generation. Inhibition of JNK signalling may be observed by the use of a JNK reporter construct in said cell. One widely used reporter is an AP-1 promoter driven reporter.

A cell to be used in the described method of the invention is preferably a mammalian, most preferably a human cell. It is also preferred that the cell is an immune cell, most preferably a leucocyte, even more preferably a macrophage.

Yet another aspect of the invention relates to a method for screening for modulators of the activity of truncated IL-38, comprising the steps of
  a. Providing a cell,
  b. Contacting said cell with microbe-associated molecular pattern (MAMP), pathogen-associated molecular patterns (PAMP) or apoptotic cell supernatants (ACM),
  c. Further contacting said cell with a truncated IL-38 protein of the invention and a candidate modulator,
  d. Determining JNK activation in said cell,
wherein an increase of JNK activation in said cell compared to a control cell or reference value indicates that the candidate modulator is an antagonist of truncated IL-38, and a decrease of JNK activation compared to a control cell or reference indicates that the candidate modulator is an agonist of truncated IL-38.

PAMPs or MAMPs in accordance with the invention may be selected from bacterial lipopolysaccharide (LPS), bacterial flagellin, lipoteichoic acid from Gram positive bacteria, peptidoglycan, and nucleic acid variants normally associated with viruses, such as double-stranded RNA (dsRNA), or unmethylated CpG motifs.

Said cell to be used in the screening method of the invention preferably expresses on the cell surface a receptor of truncated IL-38, for example by ectopically expressing IL-1RAPL1 in said cell.

A candidate modulator is preferably a small molecule, a small nucleic acid, such as a small RNA, or a protein, such as an antibody.

Said JNK activation is preferably determined by means of an AP-1 reporter construct. Such reporter constructs may be luciferase based, enzyme based or fluorescent protein based. Also the direct JNK target gene expression may be determined, for example by quantitative PCR (qPCR).

Furthermore the invention provides a modulator of the activity of truncated IL-38 as identified by the herein described method.

Diseases and Conditions

The present invention provides a truncated IL-38 protein which can be used as a therapeutic in the treatment or prevention of various diseases. In accordance with the present invention the compounds and compositions are particularly useful for the treatment and or prevention of a condition characterized by a pathological activated immune or inflammatory response. In particular the invention seeks to provide a treatment for conditions characterized by a pathological activity of cytokines such as interleukin-6 and interleukin-17, which were shown to be involved in a wide series of chronic inflammatory and autoimmune disorders.

In context of the present invention an autoimmune disease is as a disorder that results from an autoimmune response. An autoimmune disease is the result of an inappropriate and excessive response to a self-antigen, or a pathological activation of immune response signalling for example via cytokines. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

Compositions and Kits for Treating or Preventing Autoimmune Diseases

Another aspect of the present application relates to compositions and kits for treating or preventing autoimmune or inflammatory diseases. In one embodiment, the composition comprises a compound such as a protein, nucleic acid, or recombinant cell as described herein, optionally together with a pharmaceutically acceptable carrier.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neuregulin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: IL-38 is secreted from apoptotic cells. (A) A549 human lung cancer cells, MDA-231 breast cancer cells, human primary PBMCs and human primary neutrophils remained viable, were treated with TNF-alpha (20 ng/ml)/CHX (10 µM) to include apoptosis or were incubated at 60° C. for 30 min to induce necrosis. Respective supernatants of viable (VCM), apoptotic (ACM) or necrotic (NCM) cells were harvested and IL-38 levels were analyzed by ELISA. Data are means±SEM, n=5. (B) Secretion of IL-38 from apoptotic A549 cells was analyzed by ELISA at the times indicated. Data are means±SEM, n=5. *p<0.05, ANOVA with Bonferroni's correction.

Figure 2:
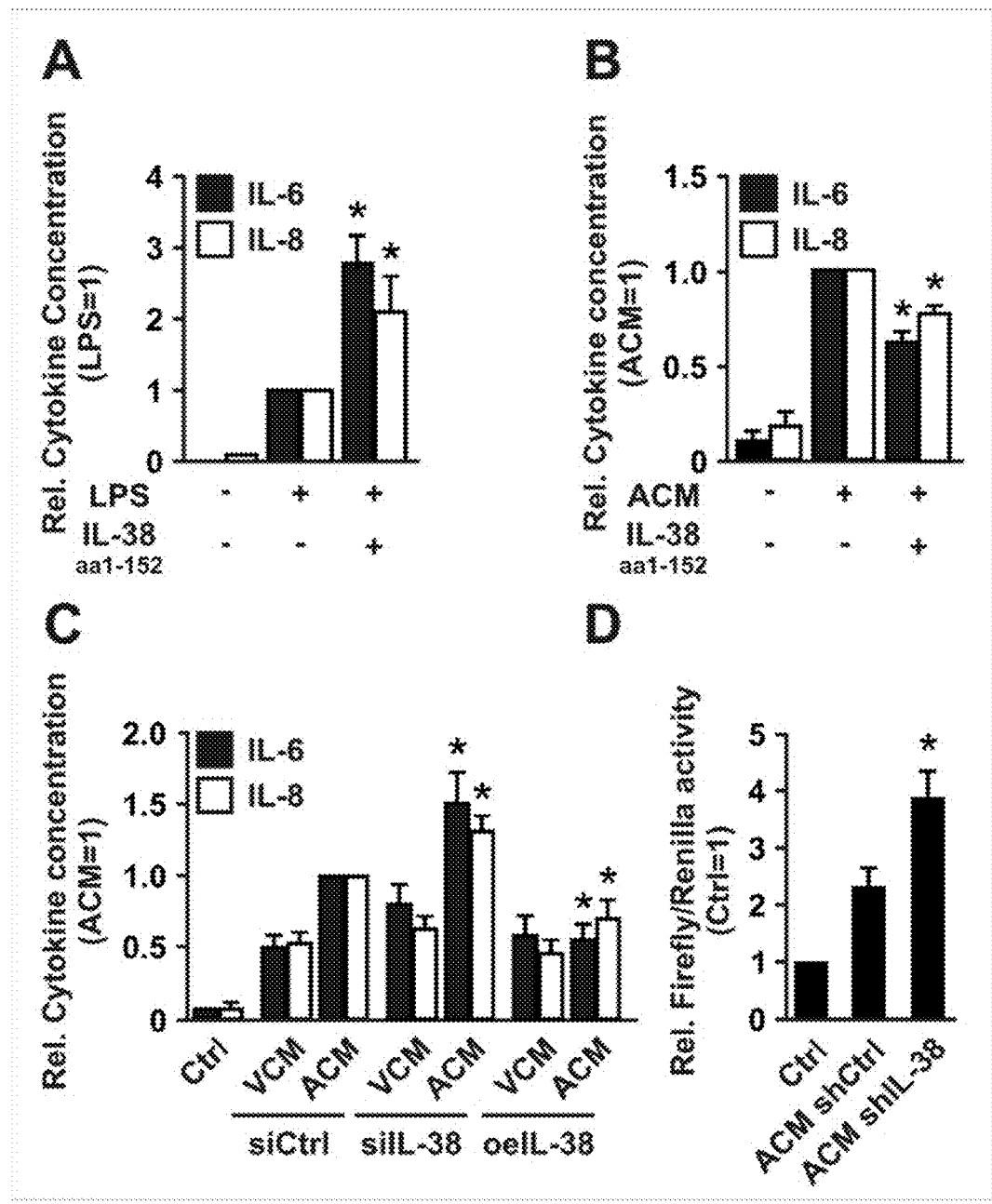

FIG. 2: Apoptotic tumor cell-released IL-38 regulates cytokine production in macrophages. Human macrophages were stimulated for 24 h with (A) LPS (1 ng/ml) alone or in combination with recombinant human IL-38 (rhIL-38) long/ml or with (B) supernatants of apoptotic A549 cells (ACM) alone or in combination with recombinant human IL-38 (rhIL-38) 10 ng/ml. Cytokine production was measured using cytometric bead array, normalized results are shown. Data are means±SEM, n=5 (C) Human macrophages were stimulated with supernatants of viable (VCM) or apoptotic A549 cells (ACM), which were previously transfected with non-targeting siRNA (siCtrl), siRNA directed against IL-38 (siIL-38) or an IL-38 overexpression vector (oeIL-38). Cytokine production was measured using cytometric bead array, normalized results are shown. Data are means±SEM, n=5 (D) Human macrophages were transfected with an AP1 reporter construct and luciferase activity was measured after 24 h stimulation with ACM from siCtrl and siIL-38 A549 cells. Background measurements obtained from mock-transfected cells were subtracted from each experimental value. Normalized results are shown. Data are means±SEM, n=5.*p<0.05, ANOVA with Bonferroni's correction.

Figure 3:
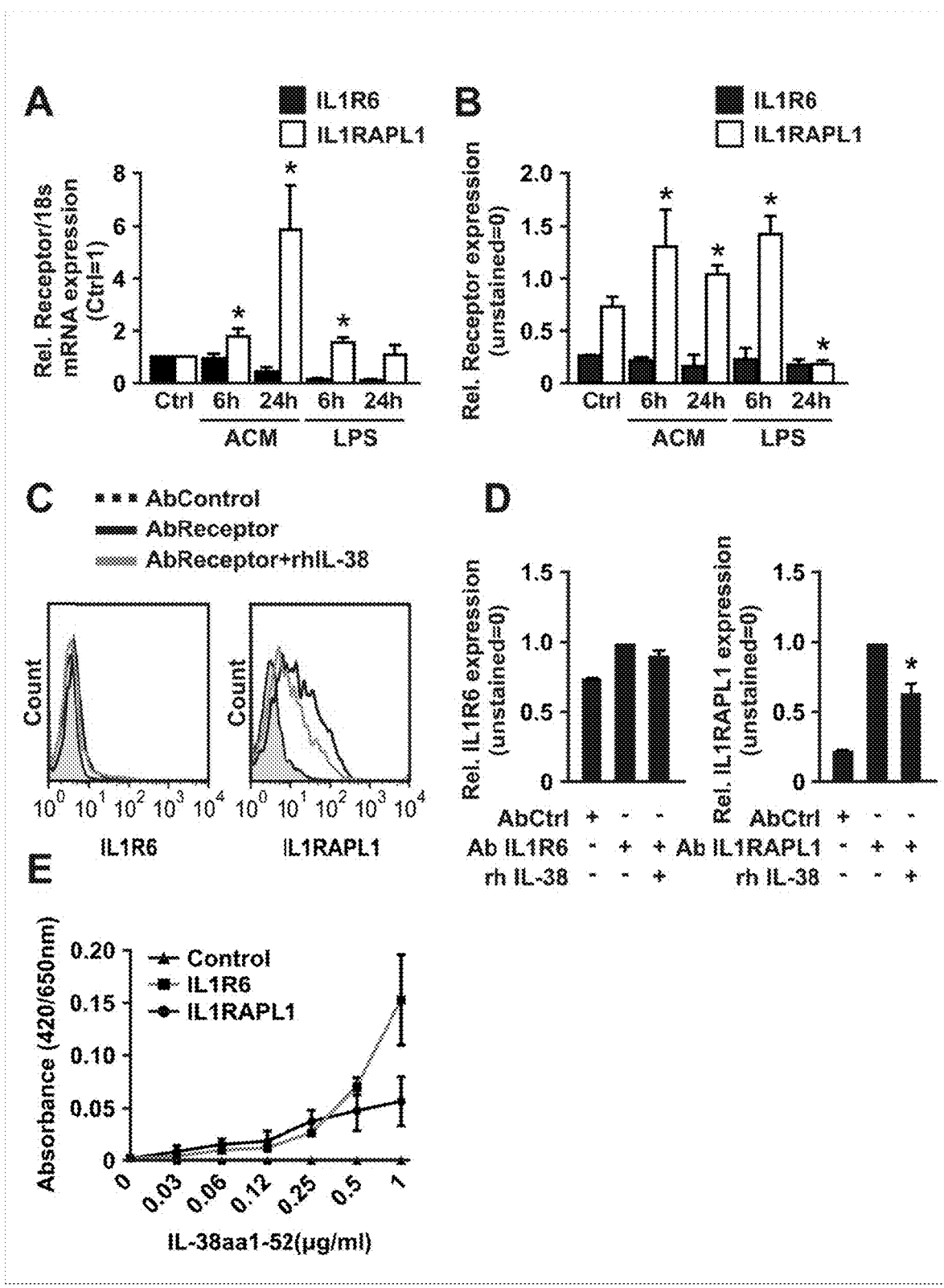

FIG. 3: IL-38 binds to IL-1R6 and IL-1RAPL1. (A,B) Human macrophages were stimulated with LPS or ACM for 6 and 24 h. mRNA expression (A) and cell surface protein expression (B) of IL-1R6 and IL-1RAPL1 were measured by RT-qPCR and FACS respectively. Data are means±SEM, n=5. (C,D) Macrophages were controls (Ctrl) or incubated with 50 ng/ml IL-38 for 15 min on ice before staining with anti-IL-1R6 or anti-IL-1RAPL1 and their respective PE-conjugated secondary antibodies. Representative flow cytometry histograms (C) and statistical quantification of median PE intensity (D) are displayed. Data are means±SEM, n=5. (E) Binding kinetics of IL-38 to immobilized IL-1R6 and IL-1RAPL1. 96 well plates were coated with 0.5 µg of human IL-1R6 and IL-1RAPL1 extracellular domain-Fc chimeras and incubated with increasing amounts of human recombinant IL-38 as indicated. IL-38 binding to the extracellular domain of the receptors was detected using biotinylated monoclonal IL-38 antibody. Data are means±SEM, n=5.*p<0.05, ANOVA with Bonferroni's correction.

Figure 4:
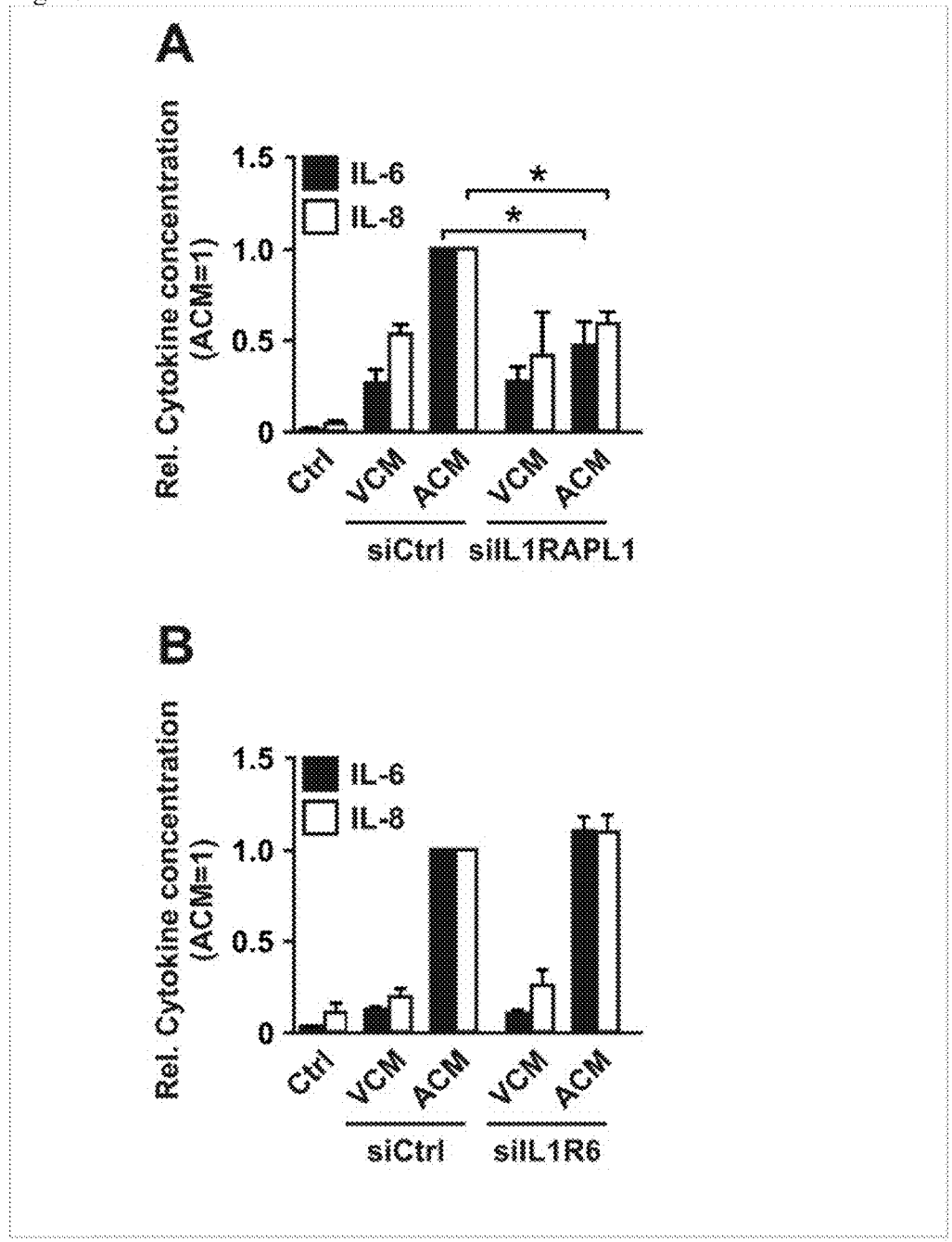

FIG. 4: Role of IL-1R6 and IL-1RAPL1 in cytokine production. Human macrophages were transfected with non-targeting siRNA (siCtrl) or siRNA directed against (A) IL-1RAPL1 (siIL1RAPL1) or (B) IL-1R6 (siIL1R6) and stimulated with VCM and ACM for 24 h. Cytokine production was measured using cytometric bead array, normalized results are shown. Data are means±SEM, n=5. *p<0.05, ANOVA with Bonferroni's correction.

Figure 5:
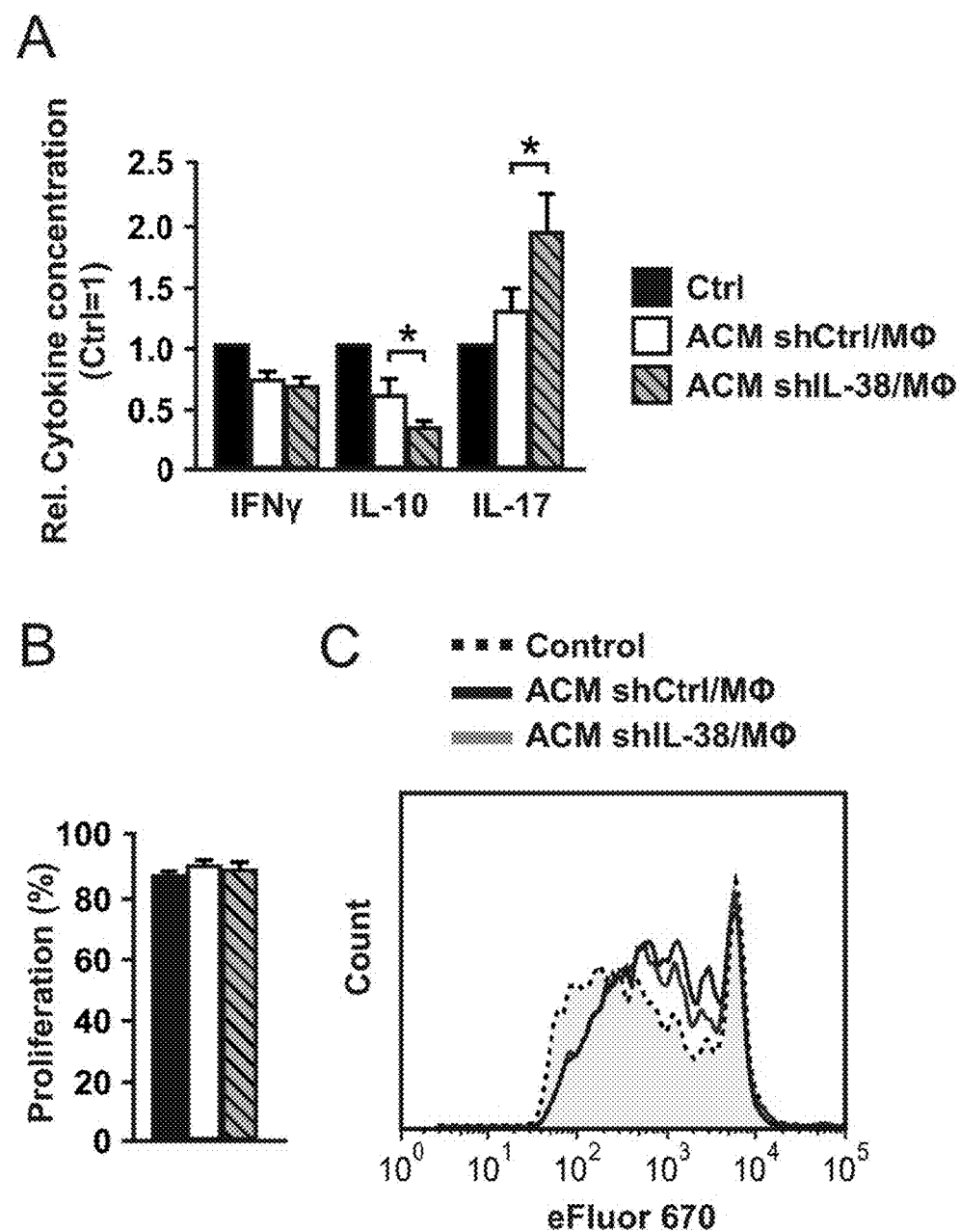

FIG. 5: IL-38 regulates the Th17 response. Human T-cells were activated with anti-CD3/anti-CD28 beads, stained with eFluor 670 and stimulated with the supernatant of macrophages previously stimulated with ACM from control A549 cells (ACMshCtrl/MΦ) or IL-38 knock-down A549 cells (ACMshIL-38/MΦ). After 7 days (A) cytokine production and (B,C) cell proliferation was measured. (A) Cytokines were quantified using cytometric bead array, normalized results are shown. Data are means±SEM, n=10. T-cell proliferation was determined by following eFluor 670 dilution. (B) Statistical quantification of all proliferating T cells and (C) representative flow cytometry histograms are displayed. Data are means±SEM, n=10. *p<0.05, ANOVA with Bonferroni's correction.

Figure 6:
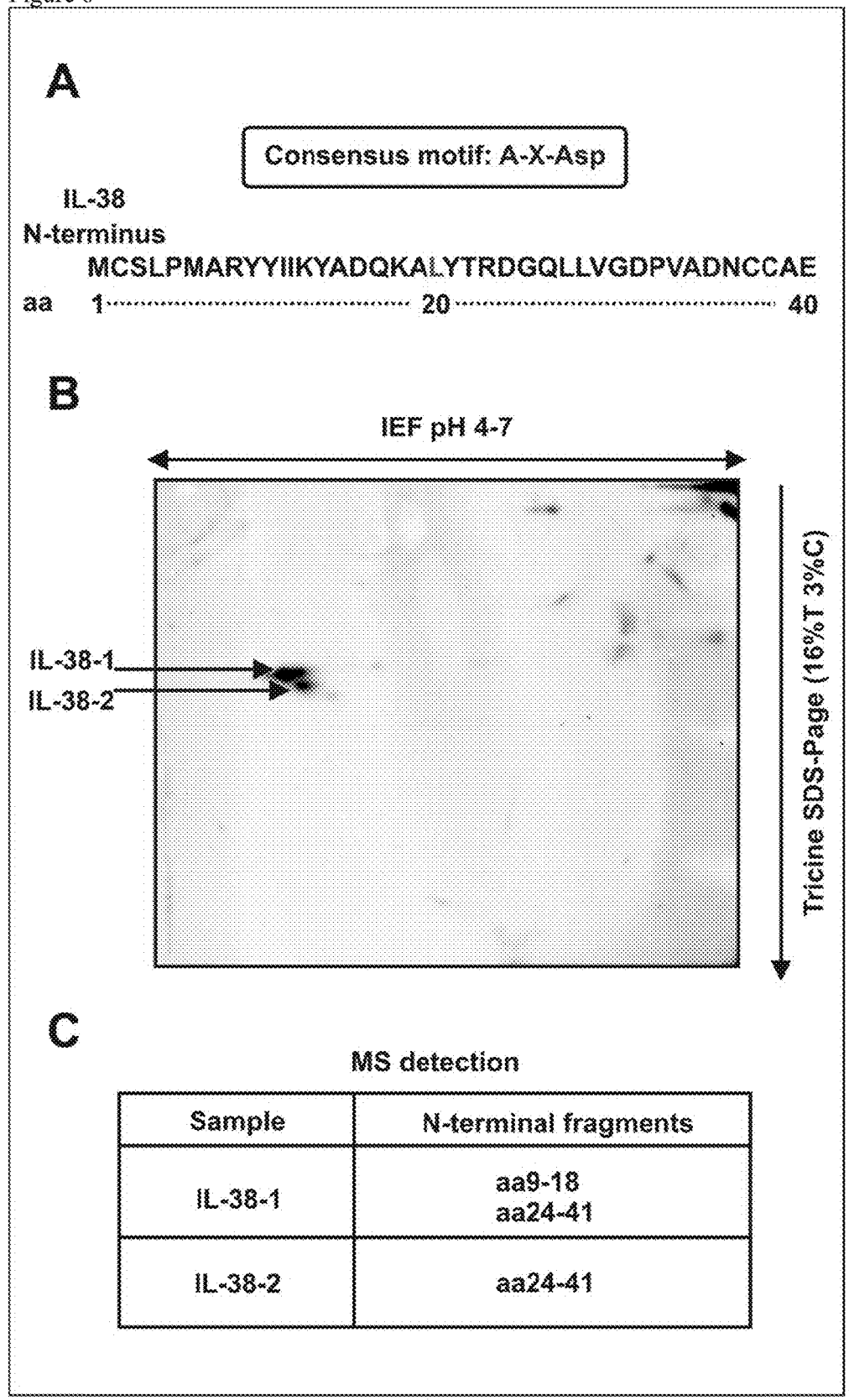

FIG. 6: IL-38 is truncated at the N-Terminus. (A) The characteristic consensus motif of the IL-36 family in IL-38, which defines the putative cleavage site of this cytokine at the N-terminus, is displayed. (B) C-terminally myc-tagged IL-38 was over-expressed in A549 cells, which were then used for ACM production. After immunoprecipitating the over-expressed IL-38 using anti-myc coated beads, 2D gel electrophoresis was performed (isoelectric focusing at pH 4-7, followed by polyacrylamide gel separation), and a monoclocal anti-myc antibody was used to detect the immunoprecipitated IL-38 upon protein transfer onto nitrocellulose. (C) Coomasie-stained 2D gels were used for picking putative IL-38 spots, which were analyzed by mass spectrometry. Identified IL-38 N-terminal peptides for the different IL-38 spots are displayed.

Figure 7:
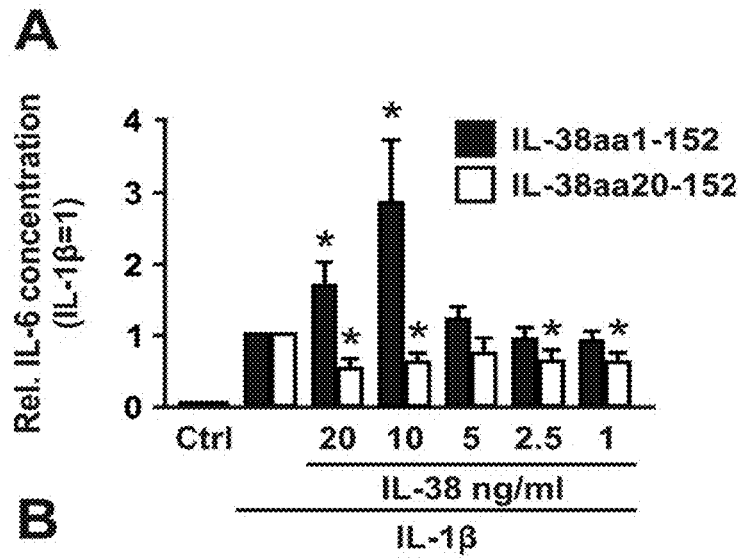
Figure 7:
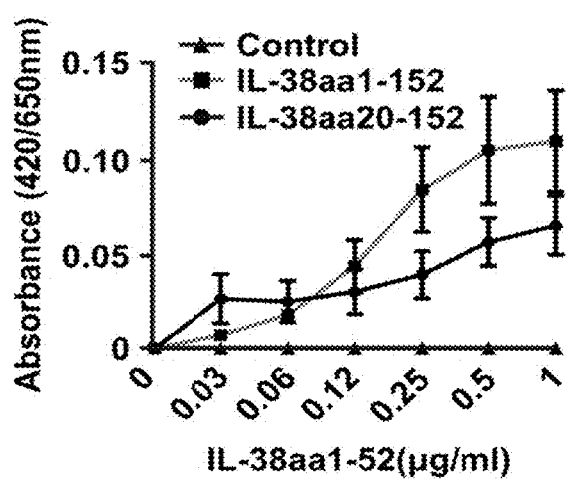
Figure 7:
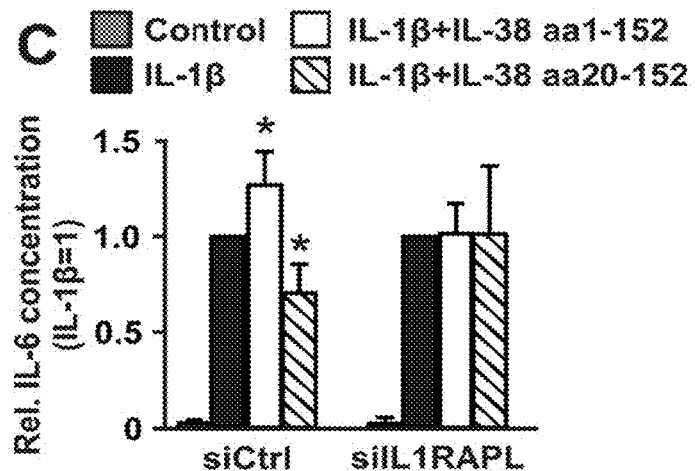

FIG. 7: Full length and truncated IL-38 have opposite roles in cytokine production and bind to IL-1RAPL1. (A,C) Human macrophages were (A) untreated or (C) previously transfected with non-targeting siRNA (siCtrl) or siRNA directed against IL-1RAPL1 (siIL1RAPL1) and stimulated for 6 h with recombinant human IL-1β 50 ng/ml alone or in combination with different concentrations of recombinant human full length (IL-38aa1-152) or cleaved (IL-38aa20-152) IL-38. After 24 h IL-6 concentration in the supernatants was measured using cytometric bead array, normalized results are shown. Data are means±SEM, n=7. (B) Binding kinetics of full length and cleaved IL-38 to immobilized IL-1RAPL1. 96 well plates were coated with 0.5 µg of human IL-1RAPL1 extracellular domain-Fc chimeras and incubated with increasing amounts of human recombinant IL-38aa1-152 or IL-38aa20-152 as indicated. IL-38 binding to the extracellular domain of the receptors was detected using biotinylated monoclonal IL-38 antibody. Data are means±SEM, n=5.*p<0.05, ANOVA with Bonferroni's correction.

Figure 8:
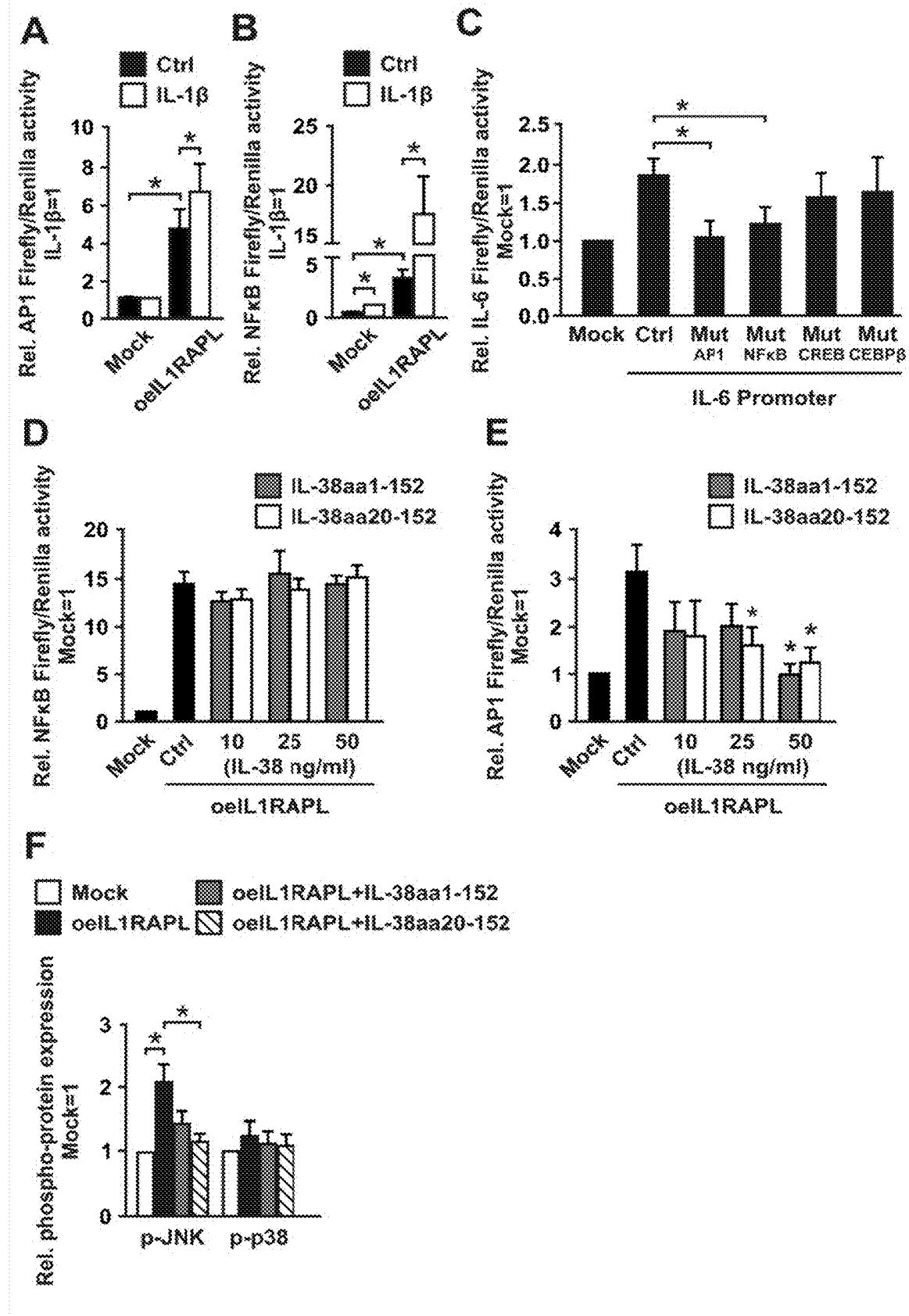

FIG. 8: IL-1RAPL1-induced signalling pathways regulated by IL-38 in HEK cells. HEK cells were co-transfected with an IL-1RAPL1 over-expression plasmid in combination with (A,D) AP1, (B,E) NFκB or (C) IL-6 reporter constructs. HEK cells transfected with the reporter constructs together with an empty plasmid instead the IL-1RAPL1 overexpression plasmid were used as controls (Mock). (A,B) HEK cells were stimulated with IL-1β (50 ng/ml) for 24 h and the AP1 or NFκB activity was measured. Normalized results are shown. Data are means±SEM, n=15. (C) IL-6 reporter constructs with point mutations in the indicated transcription binding sites were used. After transfection, cells were incubated for additional 24 h and IL-6 promoter-dependent luciferase activity was measured. Results are expressed as fold induction relative to Mock transfected cells. Data are means±SEM, n=10. (D,E) After transfection, fresh medium (Ctrl) or different concentrations of IL-38aa1-152 or IL-38aa20-152 were added and cells were incubated for additional 24 h. Results are expressed as fold induction relative to Mock transfected cells. Data are means±SEM, n=15. (F) IL1RAPL1 was overexpressed in HEK cells and after transfection fresh medium (Ctrl) or IL-38aa1-152 or IL-38aa20-152 (25 ng/ml) were added to the cells followed by incubation for additional 24 h. Intracellular staining of phosphorylated JNK and p38 was performed and measured by FACS. Results are expressed as fold induction relative to Mock transfected cells. Data are means±SEM, n=5. *p<0.05, ANOVA with Bonferroni's correction.

Figure 9:
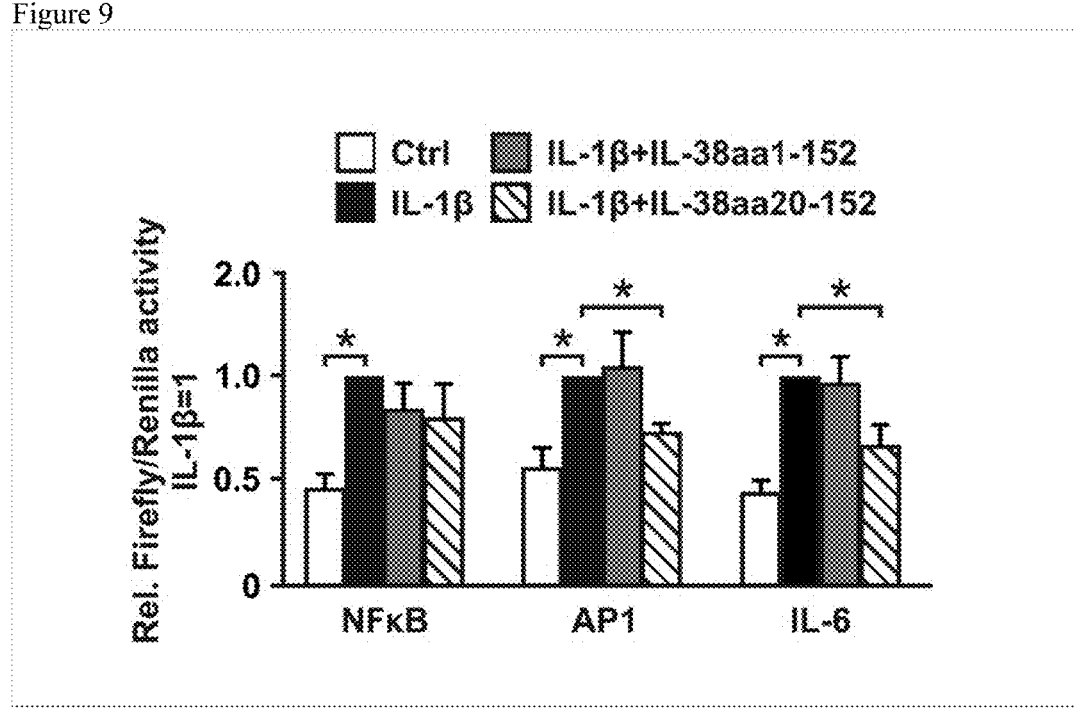

FIG. 9: IL-38 regulates AP1 activity in macrophages. Human macrophages were transfected with an empty vector, AP1, NFκB or IL-6 reporter constructs. After transfection, macrophages were stimulated for 24 h with IL-1β (50 ng/ml) alone or in combination with IL-38aa1-152 or IL-38aa20-152 (20 ng/ml). Luciferase activity was measured. Background measurements obtained from mock-transfected cells were subtracted from each experimental value. Normalized results are shown. Data are means±SEM, n=7. *p<0.05, ANOVA with Bonferroni's correction.

SEQ ID NO: 1
MCSLPMARYYIIKYADQKALYTRDGQLLVGDPVADNCCAEKICILPNRG

LARTKVPIFLGIQGGSRCLACVETEEGPSLQLEDVNIEELYKGGEEATR

FTFFQSSSGSAFRLEAAAWPGWFLCGPAEPQQPVQLTKESEPSARTKFY

FEQSW

SEQ ID NO: 2
LYTRDGQLLVGDPVADNCCAEKICILPNRGLARTKVPIFLGIQGGSRCL
ACVETEEGPSLQLEDVNIEELYKGGEEATRFTFFQSSSGSAFRLEAAAW
PGWFLCGPAEPQQPVQLTKESEPSARTKFYFEQSW

EXAMPLES

Example 1: IL-38 is Released from Apoptotic Cells

When performing an in-house ELISA to determine IL-38 levels produced by tumor cell lines, the inventors noticed that induction of apoptotic cell death markedly increased IL-38 secretion into the supernatant. Compared to the supernatant of viable A549 lung cancer or MDA.231 breast cancer cells (VCM), apoptotic cell supernatants (ACM), but not necrotic cell supernatants (NCM) contained approximately 10 fold higher levels of IL-38 (FIG. 1A). This was also the case for primary human neutrophils or PBMCs, although the increase of IL-38 release during apoptosis was not as strong (FIG. 1A). In order to analyze the kinetics of IL-38 secretion, the concentration of IL-38 in A549 supernatants was measured at different time points upon apoptosis induction. Enhanced IL-38 secretion was observed after 12 h following apoptosis induction (FIG. 1B), coinciding with the occurrence of apoptosis markers in A549 cells (data not shown).

Example 2: IL-38 Regulates Cytokine Production after ACM Stimulation

Apoptotic cell-derived mediators have the potential to modulate phagocyte responses, including cytokine production (26). The inventors analyzed the role of IL-38 in the production of a panel of cytokines that are produced upon macrophage activation by LPS or upon interaction with apoptotic cells (27). Of these, IL-6 and IL-8 production were regulated by IL-38. Addition of recombinant IL-38 to LPS-stimulated macrophages increased IL-6 and IL-8 production compared with LPS alone (FIG. 2A). Interestingly, when human macrophages were stimulated with ACM of A549 cells alone or in combination with recombinant human IL-38, the opposite effect was observed (FIG. 2B). IL-38 suppressed ACM-induced IL-6 and IL-8 secretion from macrophages. Since ACM already contained IL-38, the inventors wondered whether endogenous IL-38 affected cytokine macrophage cytokine production. To answer this question, IL-38 was over-expressed or knocked down in A549 cells before generating ACM. Indeed, stimulation of human macrophages with ACM produced from IL-38-overexpressing A549 cells resulted in reduced secretion of IL-6 and IL-8, whereas stimulation with ACM of IL-38 knockdown A549 cells yielded higher IL-6 and IL-8 concentrations (FIG. 2C). Among the prominent transcription factors that regulate cytokine production and are regulated by the IL-1 family are NFκB and AP1. As NFκB is blocked after interaction of macrophages with apoptotic cells (28), the inventors asked whether endogenous IL-38 regulated AP1 activation in response to ACM. When applying ACM of IL-38 knock-down A549 cells in comparison to control ACM to macrophage transfected with an AP1 luciferase reporter construct, the inventors noticed that ACM containing lower levels of IL-38 induced a more pronounced AP1 activation (FIG. 2D). In conclusion, endogenous IL-38 restricted inflammatory macrophage activation in response to apoptotic cell supernatants.

Example 3: IL-38 Antagonizes IL1RAPL1-Dependent Cytokine Production in Response in ACM The inventors hypothesized that IL-38 inhibits ACM-induced cytokine production by acting as a receptor antagonist. Therefore, the inventors analyzed candidates of the IL-1 receptor family for their association with IL-38. It was shown that IL-38 binds to the IL-1R6 (19) and the inventors observed that the orphan receptor IL-1RAPL1 regulates cytokine production in macrophages after ACM stimulation (16). The inventors first determined the expression of IL1R6 and IL-1RAPL1 in macrophages was determined at mRNA level using qPCR (FIG. 3A) and at the level of cell surface availability by FACS (FIG. 3B) after ACM or LPS stimulation. IL1R6 expression was generally low (FIG. 3C) and was further down-regulated at the mRNA level after ACM or LPS stimulation, which was nevertheless not apparent at the cell surface expression level. Contrarily, IL-1RAPL1 expression was abundant (FIG. 3C) and was further induced both at the mRNA level as well as on the cell surface at 6 h following LPS and at 6 h and 24 h following ACM treatment (FIG. 3A, B). Moreover, IL-1RAPL1 expression at the cell surface was reduced after 24 h stimulation with LPS. These experiments suggested IL-1RAPL1 at least as an additional candidate for the action of IL-38. Next, the inventors analyzed whether IL-38 would bind to IL-1RAPL1 by performing both competition assays and receptor binding assays. For competition assays, human macrophages were incubated with recombinant human IL-38 before analyzing surface expression of IL-1R6 or IL-1RAPL1. Based on the low level of IL-1R6 surface expression, it was difficult to see to observe differences in cell surface expression due to IL-38 pre-incubation (FIG. 3C, D). However, for IL-1RAPL1 the inventors observed that IL-38 competed with the antibody used for the FACS staining (FIG. 3C, D), indicating that IL-38 may bind to IL-1RAPL1. To validate these results, direct receptor binding assays were performed. Plates were coated with IL-1R6-Fc and IL-1RAPL1-Fc chimeras, different IL-38 concentrations were added to the wells and the bound IL-38 was visualized. As shown recently (19) IL-38 indeed bound to IL-1R6 (FIG. 3E). Moreover, IL-38 also bound to IL-1RAPL1 (FIG. 3E). As these results suggested that IL-38 might regulate cytokine production by binding to IL-1RAPL1, the inventors asked for the role of IL-1RAPL1 in ACM-induced cytokine production. Transient knock-down of IL-1R6 or IL-1RAPL1 was performed in human macrophages and IL-6 and IL-8 levels in macrophage culture supernatants were measured after ACM stimulation. IL-6 and IL-8 production after ACM stimulation were IL-1RAPL1 dependent (FIG. 4A), whereas IL-1R6 was not involved in cytokine production in the inventor's model (FIG. 4B).

Example 4: IL-38 Regulates Th17 Responses

Next the inventors asked for downstream consequences of IL-38-dependent suppression of cytokine production from macrophages by analyzing the effect of macrophages supernatants on T cell activation. The inventors isolated primary human T-cells, stimulated them with anti-CD3/antiCD28 beads and incubated them repeatedly with supernatants of macrophages previously stimulated with ACM and with ACM of IL-38 knock-down A549 cells. IL-10, IL-17 and IFN-γ levels were measured in the supernatants of the T-cells after seven days of culture. When macrophages were stimulated with ACM, their supernatants reduced IFN-γ and IL-10 production by T cells and slightly elevated IL-17 levels (FIG. 5A). Nevertheless, when macrophages were stimulated with ACM lacking IL-38, their supernatants strongly elevated IL-17 production by T cells and further decreased IL-10 concentrations (FIG. 5A). These effects were independent of differences in T cell proliferation. Treatment with ACM did not affect the number of proliferating T cells (FIG. 5B), although it affected the number of divisions pre dividing T cells, which might explain the reduced IFN-γ and IL-10 levels (FIG. 5C). However, there was no difference in T cell proliferation whether ACM contained IL-38 or not (FIG. 5B, C). These data show that IL-38 from apoptotic cells restricts the macrophage-dependent generation of Th17 cells and maintains IL-10 expression.

Example 5: IL-38 is N-Terminally Processed in Apoptotic Cells

Except for IL-1Ra all members of the IL-1 family are produced as precursors, which need to be cleaved at the N-terminus in order to reach full activity. Recently, according to the size of the N-terminal pro-domain, IL-38 was classified into the IL-36 subfamily (4, 19). IL-38, as the other members of this subfamily, possesses a consensus motif, which putatively determines the N-terminal cleavage site (FIG. 6A). In order to determine whether or not apoptosis induced IL-38 processing, C-terminally myc-tagged IL-38 was overexpressed in tumor cells and ACM was produced from these cells. After immunoprecipitating IL-38 2D gel electrophoresis was performed to visualize IL-38 isoforms. Two IL-38 isoforms were successfully identified in the gel, indicating that IL-38 is indeed processed during apoptosis (FIG. 6B). The two spots representing putative IL-38 isoforms were picked and analyzed by mass spectrometry (MS). In the spot with higher molecular weight, predicted as full length IL-38, two N-terminal peptides were found in the MS analysis, one from amino acid 9 to 18, and the second one from amino acid 24 to 41, whereas in the sample with lower molecular weight only the peptide from amino acid 24 to 41 was found (FIG. 6C). Thus, IL-38 is N-terminally processed in apoptotic cells.

Example 6: Full Length and Truncated IL-38 Exert Opposite Roles on the Regulation of Cytokine Production Through IL-1RAPL1

In order to determine whether full-length and truncated IL-38 have a different biological activity, IL-6 concentration in the supernatants of human macrophages stimulated with IL-1β, alone or in combination with different concentrations of the full-length (IL-38aa1-152) or truncated (IL-38aa20-152) IL-38, was determined. After IL-β stimulation, higher concentrations of IL-38aa1-152 (20 ng/ml, 10 mg/ml) significantly increased IL-6 production, whereas IL-38aa20-152 decreased IL-6 production even when applied at low concentration (FIG. 7A). Since IL-38 in ACM regulated IL-6 production by interacting with IL-1RAPL1, the inventors asked whether both IL-38 isoforms, which have opposite roles in cytokine production, bind to IL-1RAPL1. The inventors performed a receptor binding assay as explained above. Both IL-38 isoforms bound to IL-1RAPL1 in this assay (FIG. 7B). However, binding kinetics seemed to differ slightly. When considering that even though IL-38aa1-152 and IL-38aa20-152 exert opposite roles on cytokine production, they are both able to bind to IL-1RAPL1, another key point to analyze was whether or not the effects on IL-6 production were both IL-1RAPL1 dependent. To achieve this, a transient IL-1RAPL1 knock-down was performed in macrophages and IL-6 concentration in the supernatants was measured after stimulation with IL-1β alone or in combination with IL-38aa1-152 or IL-38aa20-152. IL-1RAPL1 knock-down in macrophages abrogated both, IL-6 induction by full-length 11-38 and IL-6 suppression by truncated IL-38 (FIG. 7C).

Example 7: IL-38 Regulates the IL-1RAPL1-Activated Pathway JNK/AP1

The inventors obtained evidence that IL-38 regulates AP.-1 in macrophages upon interaction with apoptotic cells (FIG. 2D). To analyze the signaling pathways that are affected by IL-38 in relation to its interaction with IL-1RAPL1, the inventors first utilized a receptor-over-expression model with HEK 293T cells. The cells were co-transfected with an over-expression construct for IL-1RAPL1 and AP1 or NFκB reporter constructs. HEK cells transfected with the reporter constructs but without over-expression of IL-1RAPL1 were used as control. First, to characterize the model IL-1RAPL1 over-expressing cells and control cells were stimulated with IL-1β, and AP1 (FIG. 8A) or NFκB (FIG. 8B) activity was measured. IL-1β was used as a low-affinity ligand for the orphan receptor IL-1RAPL1 (14). After IL-1β stimulation, a significant induction of NFκB but not AP1 activity was observed in control cells. Nevertheless, when IL-1RAPL1 was overexpressed an activation of AP1 as well as enhanced NFκB activity was observed. Thus, IL-1β alone induces NFκB activation in an IL-1RAPL1-independent manner, but not AP1 activation, which required IL-1RAPL1. Interestingly, even without any stimulus, the presence of IL-1RAPL1 was sufficient to increase of AP1 and NFκB activities compared to control cells (FIG. 8A,B). IL-1RAPL1 therefore activates AP1, but not for NFκB, after IL-1 β stimulation in HEK cells, but induces AP1 and NFκB activation upon overexpression without addition of an exogenous ligand. To confirm this, IL-6 promoter constructs with or without point mutations in different transcription factor binding sites (AP1, NFκB, CREB and CEBPβ) were used. HEK cells were co-transfected with an IL1RAPL1 over-expression plasmid and IL-6 reporter constructs (29). Also in this set-up, over-expression of IL-1RAPL1 activated the IL-6 promoter compared with HEK control cells. This IL-6 promoter induction was abrogated when the AP1 and NFκB binding sites were mutated (FIG. 8C). This suggests the presence of an endogenous ligand for IL-1RAPL1 that produced by HEK cells. Next the inventors asked whether IL-38aa1-152 and IL-38aa20-152 were able to affect AP1 and NFκB activity downstream of IL-1RAPL1. NFκB promoter activity in this set-up was not regulated by IL-38 (FIG. 8D), but AP1 induction was negatively regulated by both IL-38 isoforms (FIG. 3E). Importantly, IL-38aa20-152 was able to regulate the AP1 induction at lower concentrations compared to the full-length protein. To analyze the signaling pathways leading to IL-38-dependent suppression of IL-1RAPL-induced AP1 activity, intracellular staining of phosphorylated JNK and p38 was performed in IL-1RAPL1 over-expressing cells compared with control HEK cells. After IL-1RAPL1 over-expression an induction in phosphorylated JNK but not p38 was observed. This induction was significantly reduced by IL-38aa20-152 but not by IL-38aa1-152, confirming the stronger regulatory role of truncated IL-38.

Example 8: IL-38 Regulates AP1 Activity in Macrophages

Next, the inventors transferred the inventor's data from the HEK model into the macrophage setting. Human macrophages were transfected with AP1 or NFκB reporter constructs and stimulated with IL-1β alone or in combination with IL-38aa20-152 or IL-38aa1-152. As in HEK cells, IL-38aa20-152 decreased AP1, but not NFκB activity in macrophages, whereas IL-38aa1-152 was ineffective (FIG. 9). Thus, only truncated IL-38 suppressed AP-1 activity in macrophages, which is in concordance with the inventor's finding that macrophages stimulated with apoptotic cell supernatants lacking IL-38 showed higher levels of AN activity (FIG. 2D). Finally the inventors approached the question, why IL-38aa1-152 increased IL-6 production after IL-1β stimulation of macrophages (FIG. 7A), whereas in the HEK cell model, IL-38aa1-152 did neither increase AN nor NFκB activation. To investigate this discrepancy macrophages were transfected with an IL-6 reporter construct and stimulated with IL-1β alone or in combination with both IL-38 isoforms. As expected, IL-38aa20-152 reduced IL-6 promoter activity, but IL-38aa1-152 did not affect IL-6 promoter induction at all (FIG. 9), suggesting that the IL-38aa1-152 mediated increase of IL-6 production was not transcriptionally regulated.

In conclusion, the present invention shows an N-terminally processed IL-38 which can be used in the clinic for limiting auto-inflammation in general or resulting, e.g., from defective interaction of macrophages with apoptotic cells.

REFERENCES

1. Sims, J. E. & Smith, D. E. (2010) Nat Rev Immunol 10, 89-102.
2. Dinarello, C. A. (2009) Annu Rev Immunol 27, 519-50.
3. Dinarello, C. A. (2013) Seminars in immunology.
4. Garlanda, C., Dinarello, C. A. & Mantovani, A. (2013) Immunity 39, 1003-18.
5. Towne, J. E., Renshaw, B. R., Douangpanya, J., Lipsky, B. P., Shen, M., Gabel, C. A. & Sims, J. E. (2011) J Biol Chem 286, 42594-602.
6. Latz, E., Xiao, T. S. & Stutz, A. (2013) Nat Rev Immunol 13, 397-411.
7. Boraschi, D. & Tagliabue, A. (2013) Seminars in immunology.
8. Pavlowsky, A., Gianfelice, A., Pallotto, M., Zanchi, A., Vara, H., Khelfaoui, M., Valnegri, P., Rezai, X., Bassani, S., Brambilla, D., Kumpost, J., Blahos, J., Roux, M. J., Humeau, Y., Chelly, J., Passafaro, M., Giustetto, M., Billuart, P. & Sala, C. (2010) Current biology: CB 20, 103-15.
9. Gambino, F., Kneib, M., Pavlowsky, A., Skala, H., Heitz, S., Vitale, N., Poulain, B., Khelfaoui, M., Chelly, J., Billuart, P. & Humeau, Y. (2009) The European journal of neuroscience 30, 1476-86.
10. Jin, H., Gardner, R. J., Viswesvaraiah, R., Muntoni, F. & Roberts, R. G. (2000) European journal of human genetics: EJHG 8, 87-94.
11. Born, T. L., Smith, D. E., Garka, K. E., Renshaw, B. R., Bertles, J. S. & Sims, J. E. (2000) The Journal of biological chemistry 275, 29946-54.
12. Carrie, A., Jun, L., Bienvenu, T., Vinet, M. C., McDonell, N., Couvert, P., Zemni, R., Cardona, A., Van Buggenhout, G., Frints, S., Hamel, B., Moraine, C., Ropers, H. H., Strom, T., Howell, G. R., Whittaker, A., Ross, M. T., Kahn, A., Fryns, J. P., Beldjord, C., Marynen, P. & Chelly, J. (1999) Nature genetics 23, 25-31.
13. Khan, J. A., Brint, E. K., O'Neill, L. A. & Tong, L. (2004) The Journal of biological chemistry 279, 31664-70.
14. Pavlowsky, A., Zanchi, A., Pallotto, M., Giustetto, M., Chelly, J., Sala, C. & Billuart, P. (2010) Commun Integr Biol 3, 245-7.
15. Arthur, J. S. & Ley, S. C. (2013) Nat Rev Immunol 13, 679-92.
16. Ley, S., Weigert, A., Heriche, J. K., Mille-Baker, B., Janssen, R. A. & Brune, B. (2013) Immunobiology 218, 40-51.
17. Lin, H., Ho, A. S., Haley-Vicente, D., Zhang, J., Bernal-Fussell, J., Pace, A. M., Hansen, D., Schweighofer, K., Mize, N. K. & Ford, J. E. (2001) The Journal of biological chemistry 276, 20597-602.
18. Bensen, J. T., Dawson, P. A., Mychaleckyj, J. C. & Bowden, D. W. (2001) Journal of interferon & cytokine research: the official journal of the International Society for Interferon and Cytokine Research 21, 899-904.
19. van de Veerdonk, F. L., Stoeckman, A. K., Wu, G., Boeckermann, A. N., Azam, T., Netea, M. G., Joosten, L. A., van der Meer, J. W., Hao, R., Kalabokis, V. & Dinarello, C. A. (2012) Proc Natl Acad Sci USA 109, 3001-5.
20. Jung, M. Y., Kang, S. W., Kim, S. K., Kim, H. J., Yun, D. H., Yim, S. V., Hong, S. J. & Chung, J. H. (2010) Scandinavian journal of rheumatology 39, 190-6.
21. Guo, Z. S., Li, C., Lin, Z. M., Huang, J. X., Wei, Q. J., Wang, X. W., Xie, Y. Y., Liao, Z. T., Chao, S. Y. & Gu, J. R. (2010) International journal of immunogenetics 37, 33-7.
22. Chou, C. T., Timms, A. E., Wei, J. C., Tsai, W. C., Wordsworth, B. P. & Brown, M. A. (2006) Annals of the rheumatic diseases 65, 1106-9.

23. Monnet, D., Kadi, A., Izac, B., Lebrun, N., Letourneur, F., Zinovieva, E., Said-Nahal, R., Chiocchia, G. & Breban, M. (2012) Annals of the rheumatic diseases 71, 885-90.
24. Rahman, P., Sun, S., Peddle, L., Snelgrove, T., Melay, W., Greenwood, C. & Gladman, D. (2006) Arthritis and rheumatism 54, 2321-5.
25. Dehghan, A., et al. (2011) Circulation 123, 731-8.
26. Zitvogel, L., Kepp, 0. & Kroemer, G. (2010) Cell 140, 798-804.
27. Ley, S., Weigert, A., Weichand, B., Henke, N., Mille-Baker, B., Janssen, R. A. & Brune, B. (2013) Oncogene 32, 631-40.
28. Weigert, A., Tzieply, N., von Knethen, A., Johann, A. M., Schmidt, H., Geisslinger, G. & Brune, B. (2007) Mol Biol Cell 18, 3810-9.
29. Xiao, W., Hodge, D. R., Wang, L., Yang, X., Zhang, X. & Farrar, W. L. (2004) Prostate 61, 354-70.

The invention claimed is:

1. An isolated truncated IL-38 protein consisting of an amino acid sequence of SEQ ID NO: 2.

\* \* \* \* \*

SEQUENCE LISTING

```
<160> NUMBER OF SEQ ID NOS: 2

<210> SEQ ID NO 1
<211> LENGTH: 152
<212> TYPE: PRT
<213> ORGANISM: Homo sapiens

<400> SEQUENCE: 1

Met Cys Ser Leu Pro Met Ala Arg Tyr Tyr Ile Ile Lys Tyr Ala Asp
1               5                   10                  15

Gln Lys Ala Leu Tyr Thr Arg Asp Gly Gln Leu Leu Val Gly Asp Pro
            20                  25                  30

Val Ala Asp Asn Cys Cys Ala Glu Lys Ile Cys Ile Leu Pro Asn Arg
        35                  40                  45

Gly Leu Ala Arg Thr Lys Val Pro Ile Phe Leu Gly Ile Gln Gly Gly
    50                  55                  60

Ser Arg Cys Leu Ala Cys Val Glu Thr Glu Gly Pro Ser Leu Gln
65                  70                  75                  80

Leu Glu Asp Val Asn Ile Glu Glu Leu Tyr Lys Gly Gly Glu Glu Ala
                85                  90                  95

Thr Arg Phe Thr Phe Phe Gln Ser Ser Ser Gly Ser Ala Phe Arg Leu
            100                 105                 110

Glu Ala Ala Ala Trp Pro Gly Trp Phe Leu Cys Gly Pro Ala Glu Pro
        115                 120                 125

Gln Gln Pro Val Gln Leu Thr Lys Glu Ser Glu Pro Ser Ala Arg Thr
    130                 135                 140

Lys Phe Tyr Phe Glu Gln Ser Trp
145                 150

<210> SEQ ID NO 2
<211> LENGTH: 133
<212> TYPE: PRT
<213> ORGANISM: Homo sapiens

<400> SEQUENCE: 2

Leu Tyr Thr Arg Asp Gly Gln Leu Leu Val Gly Asp Pro Val Ala Asp
1               5                   10                  15

Asn Cys Cys Ala Glu Lys Ile Cys Ile Leu Pro Asn Arg Gly Leu Ala
            20                  25                  30

Arg Thr Lys Val Pro Ile Phe Leu Gly Ile Gln Gly Gly Ser Arg Cys
        35                  40                  45

Leu Ala Cys Val Glu Thr Glu Glu Gly Pro Ser Leu Gln Leu Glu Asp
    50                  55                  60

Val Asn Ile Glu Glu Leu Tyr Lys Gly Gly Glu Ala Thr Arg Phe
65                  70                  75                  80

Thr Phe Phe Gln Ser Ser Ser Gly Ser Ala Phe Arg Leu Glu Ala Ala
                85                  90                  95
```

-continued

```
Ala Trp Pro Gly Trp Phe Leu Cys Gly Pro Ala Glu Pro Gln Gln Pro
            100                 105                 110

Val Gln Leu Thr Lys Glu Ser Glu Pro Ser Ala Arg Thr Lys Phe Tyr
        115                 120                 125

Phe Glu Gln Ser Trp
    130
```